(12) United States Patent
Tanaka

(10) Patent No.: US 9,517,217 B2
(45) Date of Patent: Dec. 13, 2016

(54) IMMUNE CELL ACTIVATION INHIBITOR AND USE THEREOF

(71) Applicant: EHIME UNIVERSITY, Matsuyama-shi, Ehime (JP)

(72) Inventor: Junya Tanaka, Toon (JP)

(73) Assignee: EHIME UNIVERSITY, Ehime (JP)

( * ) Notice: Subject to any disclaimer, the term of this patent is extended or adjusted under 35 U.S.C. 154(b) by 0 days.

(21) Appl. No.: 14/419,182

(22) PCT Filed: Aug. 2, 2013

(86) PCT No.: PCT/JP2013/071028
§ 371 (c)(1),
(2) Date: Feb. 2, 2015

(87) PCT Pub. No.: WO2014/021455
PCT Pub. Date: Feb. 6, 2014

(65) Prior Publication Data
US 2015/0202170 A1     Jul. 23, 2015

(30) Foreign Application Priority Data

Aug. 3, 2012 (JP) ................. 2012-173405

(51) Int. Cl.
*A61K 31/17* (2006.01)
(52) U.S. Cl.
CPC ..................... *A61K 31/17* (2013.01)
(58) Field of Classification Search
USPC ................. 514/579, 588, 613, 616
See application file for complete search history.

(56) References Cited

U.S. PATENT DOCUMENTS

| | | | |
|---|---|---|---|
| 5,409,709 A | 4/1995 | Ozawa et al. | |
| 2006/0153905 A1* | 7/2006 | Carrara ................ | A61K 9/0014 424/449 |

FOREIGN PATENT DOCUMENTS

| | | |
|---|---|---|
| EP | 2 702 989 | 3/2014 |
| JP | 11-139971 | 5/1999 |
| JP | 2004-231546 | 8/2004 |
| JP | 4787499 | 10/2011 |
| UA | 61 135 | 9/2001 |
| WO | 03/077832 | 9/2003 |
| WO | 2009/001356 | 12/2008 |

OTHER PUBLICATIONS

Mochizuki, "Treatment and pathogenesis of Parkinson's disease", Rinsho Shinkeigaku (Clinical Neurology), 2010, vol. 50, No. 9, pp. 623-627—English Abstract.
Kumar et al., "A survival benefit of combination antibiotic therapy for serious infections associated with sepsis and septic shock is contingent only on the risk of death: A meta-analytic/meta-regression study", Critical Care Medicine, 2010, vol. 38, No. 8, pp. 1651-1664.
Pieracci et al., "Management of severe sepsis of abdominal origin", Scandinavian Journal of Surgery, 2007, vol. 96, pp. 184-196.
Ballard et al., "Alzheimer's disease", Lancet, 2011, vol. 377, pp. 1019-1031.
Choudhury et al., "A cytokine mixture of GM-CSF and IL-3 that induces a neuroprotective phenotype of microglia leading to amelioration of (6-OHDA)-induced Parkinsonism of rats", Brain and Behavior, 2011, vol. 1, No. 1, pp. 26-43.
Matsumoto et al., "Accumulation of macrophage-like cells expressing NG2 proteoglycan and Iba1 in ischemic core of rat brain after transient middle cerebral artery occlusion", Journal of Cerebral Blood Flow & Metabolism, 2008, vol. 28, pp. 149-163.
Nishihara et al., "Bromovalerylurea Inhibits Activation of Macrophage and Exhibits Therapeutic Effect Against Sepsis", Journal of the Physiological Society of Japan, 2013, vol. 75, No. 2, p. 74.
Aono et al., "Potential of Outdated Hypnosedative "Bromovalerylurea" as Therapeutic Agent for Parkinson's Disease", Journal of the Physiological Society of Japan, 2013, vol. 75, No. 2, p. 73.
Proceedings of the 64th Chugoku-Shikoku District Meeting of Physiological Society of Japan (Oct. 27-28, 2012)—partial translation of the 5th and 8th Subjects of Program.
Poster Presentations, pp. 114, 176, 232, 239, 249, The 90th Annual Meeting of the Physiological Society of Japan (Mar. 27-29, 2013).
The Journal of Physiological Sciences (Proceedings of the 90th Annual Meeting, Mar. 27-29, 2013, Tokyo, Japan), 2013, vol. 63, Supplement 1, pp. S83, S151, S201, S248, S260, S277.
Konishi et al., "Novel treatment for sepsis and systemic inflammatory response syndrome with bromvalerylurea", The 90th Annual Meeting of the Physiological Society of Japan (Mar. 27-29, 2013).
Tanaka, "Agents modulating neuroprotective and neurotoxic functions of microglia and their application to the pathologic brains", The 90th Annual Meeting of the Physiological Society of Japan (Mar. 27-29, 2013).
Kawamoto et al., "Mechanisms underlying suppressive effects of bromvalerylurea on LPS-activated microglia/macrophages", The 90th Annual Meeting of the Physiological Society of Japan (Mar. 27-29, 2013).

(Continued)

*Primary Examiner* — Pancham Bakshi
(74) *Attorney, Agent, or Firm* — Hamre, Schumann, Mueller & Larson, P.C.

(57) ABSTRACT

The present invention provides a pharmaceutical that can be used widely for intractable neurological diseases, inflammatory diseases, etc. The immune cell activation inhibitor of the present invention contains bromovalerylurea or a derivative thereof. The immune cell activation inhibitor of the present invention can be used as a pharmaceutical for, for example: chronic neurological diseases such as Parkinson's disease and Alzheimer's disease; acute neurological diseases such as cerebral infarction and brain injury; and inflammatory diseases such as systemic inflammatory response syndromes.

3 Claims, 12 Drawing Sheets

(56) References Cited

OTHER PUBLICATIONS

Higaki et al., "Therapeutic Effect of Hypnosedative "Bromovalerylurea" on 6-OHDA-Induced Rat Parkinson's Disease Model: Microglial Activation Inhibitory Action", Poster Presentation for the 90th Annual Meeting of the Physiological Society of Japan (Date of Presentation: Mar. 29, 2013)—partial translation.
Ochi et al., "Analyses of structure-activity correlations of bromvalerylurea that exerts anti-inflammatory effects on LPS-activated microglial cells", The 90th Annual Meeting of the Physiological Society of Japan (Mar. 27-29, 2013).
Final Program, IARS 2013 Annual Meeting, pp. 1, 36, "Kosaka AwardsFinalists" 3A S-99, IARS 2013 Annual Meeting (May 4-7, 2013).
Final Supplement to Anesthesia & Analgesia, Abstracts of Posters presented at the 2013 Annual Meeting of the International Anesthesia Research Society, 2013, vol. 116, No. 5S, p. S99, IARS 2013 Annual Meeting (May 4-7, 2013).
Nishihara et al., "An outdated sedative bromvalerylurea ameliorates sepsisinduced respiratory failure of rats by suppressing proinflammatory reactions of alveolar macrophages", IARS 2013 Annual Meeting (May 4-7, 2013).
Japanese Journal of Pathophysiology, 2013, vol. 22, No. 2, pp. 15, 35, 38, The 23rd Meeting of the Japanese Society of Pathophysiology (Aug. 2-4, 2013)—partial translation.
Journal of the Japanese Society of Intensive Care Medicine, 2013, vol. 20, p. 296, The 23rd Meeting of the Japanese Society of Pathophysiology (Aug. 2-4, 2013).
Nishihara et al., "Alveolar Macrophage Activation Inhibitory Effect of Bromovalerylurea and Therapeutic Effect of Bromovalerylurea on Acute Respiratory Distress Syndrome", Poster Presentation for the 40th Annual Meeting of the Japanese Society of Intensive Care Medicine (Date of Presentation: Mar. 1, 2013).
Supplement to SHOCK—Injury, Inflammation, and Sepsis: Laboratory and Clinical Approaches, 2013, vol. 39, Supplement 2, p. 54, 36th Anuual Conference on Shock (Jun. 1 to 4, 2013).
Kikuchi, et al., Examination on Therapeutic Effect of Bromovalerylurea on Rat Sepsis Model, Journal of the Japan Shock Society, 2013, vol. 28, No. 1, p. 50—partial translation.
Kikuchi, et al., "Examination on Therapeutic Effect of Bromovalerylurea on Rat Sepsis Model", Journal of Japan Surgical Society, 2013, vol. 114, PS-367-2—partial translation.
International Search Report for International Application No. PCT/JP2013/071028, mailed Oct. 29, 2013—4 pages.
Extended European Search Report of the corresponding European Application No. 13826292.8, Nov. 18, 2015, 10 pages.
Kuo et al., "Psychosis associated with bromvalerylurea abuse in a patient with traumatic brain injury", General Hospital Psychiatry, 2012, vol. 34, No. 3, pp. e3-e4.
Lin et al., "Myoclonic jerks due to acute bromovalerylurea intoxication", Clinical Toxicology, 2008, vol. 46, No. 9, pp. 861-863.
Nishihara et al., "Bromovalerylurea Inhibits Activation of Macrophage and Exhibits Therapeutic Effect Against Sepsis", Journal of the Physiological Society of Japan, 2013, vol. 75. No. 2, p. 74.
Aono et al., "Potential of Outdated Hypnosedative "Bromovalerylurea" as Therapeutic Agent for Parkinson's Disease", Journal of the Physiological Society of Japan, 2013, vol. 75. No. 2, p. 73.
Journal of the Japanese Society of Intensive Care Medicine, 2013, vol. 20, p. 296, The 40th Annual Meeting of the Japanese Society of Intensive Care Medicine (Date of Presentation: Mar. 1, 2013).

\* cited by examiner

* P<0.05, bromovalerylurea (+) vs (−)

*** P<0.001, bromovalerylurea (+) vs (−)

IMMUNE CELL ACTIVATION INHIBITOR AND USE THEREOF

TECHNICAL FIELD

The present invention relates to immune cell activation inhibitors. Also, the present invention relates to neuron protective agents, pharmaceutical for neurological diseases, and pharmaceuticals for systemic inflammatory response syndromes.

BACKGROUND ART

Cerebral infarction, brain injury, Parkinson's disease, Alzheimer's disease, and the like are known as intractable neurological diseases involving neuron death. In recent years, increase in the number of patients with these diseases is seen as a problem, and the prevention and treatment of these diseases are being studied eagerly. Unfortunately, existing pharmaceuticals are not sufficiently effective. Thus, there is a demand for the development of pharmaceuticals that exhibit excellent therapeutic effects widely for these diseases.

Sepsis secondary to peritonitis or the like is known as a disease with a very high case fatality rate. However, at present, the treatment for sepsis mainly is typical intensive care for the cardiorespiratory function, and another option is just the treatment using antimicrobial agents. Under these circumstances, there is a demand for the development of fast-acting and highly effective pharmaceuticals commonly applicable to sepsis. This applies not only to sepsis but also to other systemic inflammatory response syndromes.

CITATION LIST

Non-Patent Document(s)

Non-Patent Document 1: Hideki Mochizuki, "PARKINSON BYOU NO CHIRYOU TO BYOUTAI (Treatment and pathogenesis of Parkinson's disease)", Rinsho Shinkei-gaku (Clinical Neurology), 2010; 50: pp. 623-627
Non-Patent Document 2: Kumar, A. et al., A survival benefit of combination antibiotic therapy for serious infections associated with sepsis and septic shock is contingent only on the risk of death: A meta-analytic/meta-regression study. Critical care medicine, 2011; 38: pp. 1651-1664.
Non-Patent Document 3: Pieracci, F. M. and Barie, P. S., Management of severe sepsis of abdominal origin. Scandinavian Journal of Surgery 2007; 96: pp. 184-196.
Non-Patent Document 4: Ballard, C, et al. Alzheimer's disease. Lancet, 2011; 377: pp. 1019-1031

BRIEF SUMMARY OF THE INVENTION

Problem to be Solved by the Invention

With the foregoing in mind, it is an object of the present invention to provide a pharmaceutical that can be used widely for intractable neurological diseases, systemic inflammatory response syndromes, inflammatory skin diseases, etc.

Means for Solving Problem

In order to achieve the above object, the present invention provides an immune cell activation inhibitor containing bromovalerylurea or a derivative thereof.

The present invention also provides a neuron protective agent containing the immune cell activation inhibitor according to the present invention.

The present invention also provides a pharmaceutical for a neurological disease, containing the immune cell activation inhibitor according to the present invention.

The present invention also provides a pharmaceutical for an inflammatory disease, containing the immune cell activation inhibitor according to the present invention.

Effects of the Invention

According to the present invention, activation of immune cells can be inhibited by the presence of bromovalerylurea or a derivative thereof. Because bromovalerylurea or a derivative thereof can inhibit the activation of immune cells as described above, it can be used in, for example, treatment of neurological diseases involving neuron death or treatment of inflammatory diseases. Thus, it can be said that the present invention is very useful in the field of pharmaceuticals.

BRIEF DESCRIPTION OF DRAWINGS

FIG. 1A shows the result obtained when a culture system containing microglia alone was used. FIG. 1B shows the result obtained when a co-culture system containing neurons and microglia was used.

Figure 1:
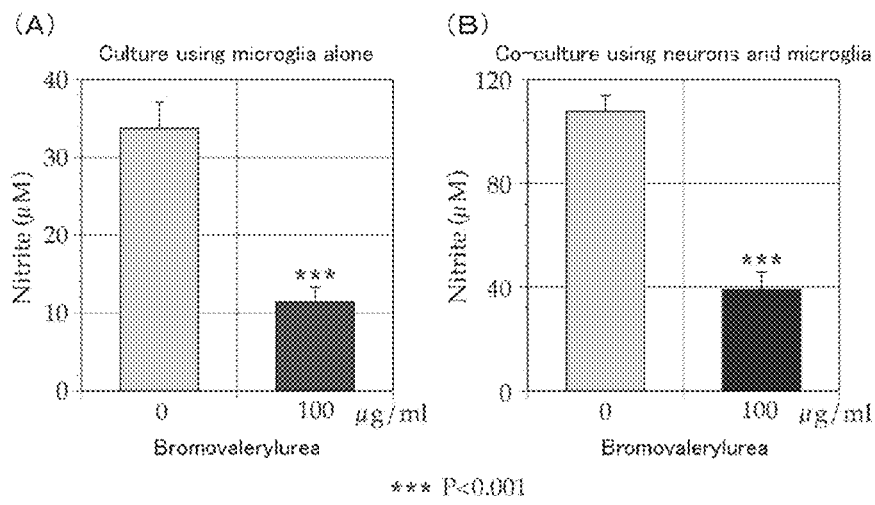
FIG. 1 shows graphs showing the amounts of nitric oxide produced in respective culture systems in Example 1.

MODE FOR CARRYING OUT THE INVENTION (Immune Cell Activation Inhibitor)

As described above, the immune cell activation inhibitor of the present invention contains bromovalerylurea or a derivative thereof.

The immune cell activation inhibitor of present invention is characterized in that it contains bromovalerylurea or a derivative thereof, and other configurations are not limited by any means. Bromovalerylurea or a derivative thereof can inhibit immune cell activation. More specifically, it can inhibit abnormal activation of immune cells, for example.

The inventor of the present invention conducted diligent studies, and as a result, he found out that bromovalerylurea can inhibit activation of various immune cells as will be described below. On the basis of this finding, he achieved the present invention. In neurological diseases involving neuron death, microglia, which are immune cells in the brain, are activated strongly. This causes nitric oxide and proinflammatory cytokines, which are both neurocytotoxic factors, to be released, whereby the death of further neurons is induced. The inventor of the present invention revealed that, as described above, bromovalerylurea can inhibit the activation of microglia or macrophages as immune cells, which means, in other words, bromovalerylurea can inhibit damages to neurons caused by the microglia or macrophages. Because bromovalerylurea can inhibit the activation of microglia or macrophages as described above, it is considered that, for example, the release of the above-described neurocytotoxic factors, namely, nitric oxide and proinflammatory cytokines, is inhibited, which results in inhibition of the neuron death induction, thereby allowing neurological diseases to be described below to be treated. Also, in systemic inflammatory response syndromes (referred to as "SIRS" hereinafter) such as sepsis, immune cells are activated abnormally. This causes various kinds of proinflammatory cytokines to be released in large amounts, which induces the state called "cytokine storm". Further, by the induction of this cytokine storm, the functions of many organs such as the lung, kidney, and heart are deteriorated rapidly, which may lead to death. Bromovalerylurea can inhibit the immune cell activation, as described above. It is thus considered that, for example, bromovalerylurea inhibits the accumulation of immune cells in an inflammatory tissue to inhibit the increase in the concentration of proinflammatory cytokines, whereby damages to organs can be reduced. The same also applies to various inflammatory diseases other than the SIRS. Bromovalerylurea is already known as a hypnosedative, for example. However, the effect of bromovalerylurea in the present invention is newly discovered by the inventor of the present invention. Also, the fact that bromovalerylurea is effective against the above-described various diseases through the above-described action mechanism is newly discovered by the inventor of the present invention. Moreover, as clear from the fact that bromovalerylurea is approved as a hypnosedative as described above, bromovalerylurea is excellent in safety and reliability.

The immune cell activation inhibitor of the present invention can be used as, for example, a neuron protective agent or a neuron death inhibitor, as will be described below. Also, the immune cell activation inhibitor of the present invention can be used as, for example, a pharmaceutical for a neurological disease and a pharmaceutical for an inflammatory disease. Examples of the immune cell include immune cells in the brain, such as microglia and macrophages.

Bromovalerylurea is represented by the following formula (1). Bromovalerylurea also is referred to as bromvalerylurea or bromisoval, for example. The bromovalerylurea may be a hydrate or a solvate, for example.

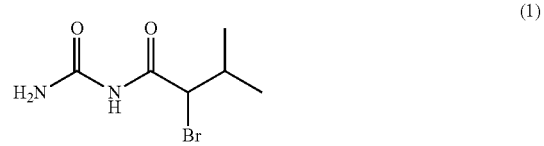

(1)

The derivative of the bromovalerylurea is not particularly limited, and examples thereof include isomers and salts of the bromovalerylurea of the formula (1). The derivative of the bromovalerylurea may be a hydrate or a solvate. Hereinafter, descriptions regarding bromovalerylurea also apply to the derivative thereof.

The immune cell activation inhibitor of the present invention may be used in vivo or in vitro, for example. The immune cell activation inhibitor of the present invention can be used as a reagent for use in research or as a pharmaceutical, for example. In the latter case, the immune cell activation inhibitor of the present invention also can be referred to as a pharmaceutical or pharmaceutical composition for inhibiting immune cell activation.

A subject to which the immune cell activation inhibitor of the present invention is administered is not particularly limited. When the immune cell activation inhibitor of the present invention is used in vivo, examples of the subject include humans and non-human animals excluding humans. Examples of the nonhuman animals include non-human mammals such as mice, rats, rabbits, dogs, sheep, horses, cats, goats, monkeys, and guinea pigs. When the immune cell activation inhibitor of the present invention is used in vitro, examples of the subject include cells, tissues, and organs. Examples of the cells include cells collected from living organisms and cultured cells.

The conditions for use of the immune cell activation inhibitor of the present invention are not particularly limited. For example, the form of administration, the timing of administration, the dose, and the like can be set as appropriate depending on the kind of the subject etc.

The amount of the immune cell activation inhibitor of the present invention to be used is not particularly limited. When the immune cell activation inhibitor of the present invention is used in vivo, the amount thereof to be used can be determined as appropriate depending on the kind of the subject, the symptom of the subject, the age of the subject, the administration method, etc., for example. As a specific example, when the immune cell activation inhibitor is administered to a human, the total daily dose of bromovalerylurea is, for example, 100 to 5000 mg, preferably 500 to 2500 mg, and the frequency of administration per day is, for example, 1 to 5 times, preferably 1 to 3 times. The content of bromovalerylurea in the activation inhibitor is not particularly limited, and can be set as appropriate depending on the above-described administration conditions, for example.

The form of administration of the immune cell activation inhibitor of the present invention is not particularly limited. When the immune cell activation inhibitor of the present invention is administered in vivo, the form of administration may be, for example, oral administration or parenteral administration. Examples of the parenteral administration include intravenous injection, intramuscular injection, subcutaneous administration, rectal administration, transdermal administration, intraperitoneal administration, and local administration.

The dosage form of the immune cell activation inhibitor of the present invention is not particularly limited, and can be determined as appropriate depending on the form of administration, for example. The dosage form may be liquid or solid, for example. In the case of oral administration, the dosage form may be, for example, a tablet, a coated tablet, a pill, a microgranule, a granule, a powder medicine, a capsule, a liquid medicine, syrup, emulsion, suspension, or the like. In the case of parenteral administration, the dosage form may be, for example, a preparation for injection, a preparation for infusion, or the like. In the case of transdermal administration, the dosage form may be, for example, a medicine for external application, such as a patch, embrocation, ointment, cream, lotion, or the like.

The immune cell activation inhibitor of the present invention may contain an additive(s) as necessary, for example. When the activation inhibitor of the present invention is used as a pharmaceutical, it is preferable that the additive is pharmaceutically acceptable. The additive is not particularly limited, and examples thereof include a base material, an excipient, a colorant, a lubricant, a binding agent, a disintegrant, a stabilizer, a preservative, and a flavoring agent such as fragrance. In the present invention, the amount of the additive to be blended is not particularly limited as long as the function of the bromovalerylurea is not hindered.

Examples of the excipient include organic excipients including: sugar derivatives such as lactose, sucrose, glucose, mannitol, and sorbitol; starch derivatives such as corn starch, potato starch, a starch, and dextrin; cellulose derivatives such as microcrystalline cellulose; gum arabic; dextran; and pullulan, and also, inorganic excipients including: silicate derivatives such as light anhydrous silicic acid, synthesized aluminum silicate, calcium silicate, and magnesium aluminometasilicate; phosphates such as calcium hydrogen phosphate; carbonate such as calcium carbonate; and sulfate such as calcium sulfate. Examples of the lubricant include metal stearates such as stearic acid, calcium stearate, and magnesium stearate; talc; polyethylene glycol; silica; and hydrogenated vegetable oils. Examples of the flavoring agent include: fragrances such as cocoa powder, menthol, aromatic powders, mentha oil, borneol, and powdered cinnamon bark; sweeteners; and acidulants. Examples of the binding agent include hydroxypropyl cellulose, hydroxypropyl methylcellulose, polyvinylpyrrolidone, and macrogol. Examples of the disintegrant include: cellulose derivatives such as carboxymethyl cellulose and carboxy methylcellulose calcium; chemically-modified starches and chemically-modified celluloses, such as carboxymethyl starch, carboxymethyl starch sodium, and cross-linked polyvinylpyrrolidone. Examples of the stabilizer include: p-hydroxybenzoate esters such as methylparaben and propylparaben; alcohols such as chlorobutanol, benzyl alcohol, and phenylethyl alcohol; benzalkonium chloride; phenols such as phenol and cresol; thimerosal; dehydroacetic acid; and sorbic acid.

(Neuron Protective Agent)

As described above, the neuron protective agent of the present invention contains the immune cell activation inhibitor of the present invention. The neuron protective agent of the present invention also can be referred to as a neuron degeneration inhibitor, for example.

The neuron protective agent of the present invention is characterized in that it contains the immune cell activation inhibitor of the present invention, i.e., it contains bromovalerylurea or a derivative thereof, and other configurations are not limited by any means. The descriptions regarding the immune cell activation inhibitor of the present invention also apply to the neuron protective agent of the present invention.

(Pharmaceutical for Neurological Disease)

As described above, the pharmaceutical for a neurological disease according to the present invention contains the immune cell activation inhibitor of the present invention.

The pharmaceutical for a neurological disease according to the present invention is characterized in that it contains the immune cell activation inhibitor of the present invention, i.e., it contains bromovalerylurea or a derivative thereof, and other configurations are not limited by any means. The descriptions regarding the immune cell activation inhibitor of the present invention also apply to the pharmaceutical for a neurological disease according to the present invention.

The pharmaceutical for a neurological disease according to the present invention can be used for prevention, treatment, and/or prognosis improvement of a neurological disease, for example. The pharmaceutical for a neurological disease according to the present invention also can be referred to as a therapeutic agent, a preventive agent, or an alleviating agent for a neurological disease, for example.

Examples of the neurological disease to which the present invention is applicable include intractable neurological diseases. Specific examples thereof include: chronic neurological diseases such as Parkinson's disease, Alzheimer's disease, amyotrophic lateral sclerosis, Huntington's disease, spinocerebellar degeneration, multiple system atrophy, and multiple sclerosis; and acute neurological diseases such as cerebral infarction, brain injury, cerebral hemorrhage, spinal cord injury, and spinal cord ischemia.

(Pharmaceutical for Inflammatory Disease)

As described above, the pharmaceutical for an inflammatory disease according to the present invention contains the immune cell activation inhibitor of the present invention.

The pharmaceutical for an inflammatory disease according to the present invention is characterized in that it contains the immune cell activation inhibitor of the present invention, i.e., it contains bromovalerylurea or a derivative thereof, and other configurations are not limited by any means. The descriptions regarding the immune cell activation inhibitor of the present invention also apply to the pharmaceutical for an inflammatory disease according to the present invention.

The pharmaceutical for an inflammatory disease according to the present invention can be used for prevention, treatment, and/or prognosis improvement of an inflammatory disease, for example. In the present invention, the inflammatory disease is not particularly limited, and examples thereof include SIRS described above and inflammatory skin diseases.

In the present invention, the term "SIRS" encompasses, for example: diseases that can cause SIRS; and diseases associated with SIRS, such as disseminated intravascular coagulation (DIC). Examples of the diseases include sepsis, septic shock associated with sepsis, acute respiratory distress syndromes (ARDS), and reactive lymphoid hyperplasia. In addition to the above diseases, examples of the diseases also include pathological conditions involving the production of large amounts of cytokines, such as thermal injury, acute pancreatitis, ischemia-reperfusion injury, surgery, and polytrauma. The pharmaceutical for an inflammatory disease according to the present invention is, for example, a pharmaceutical for SIRS, and also can be referred to as a therapeutic agent, a preventive agent, or an alleviating agent for the disease.

In the present invention, the inflammatory skin diseases are not particularly limited, and examples thereof include atopic dermatitis, contact dermatitis, psoriasis, eczema, diaper dermatitis, seborrheic dermatitis, lichen simplex chronicus Vidal, autosensitization dermatitis, senile xerosis, actinic dermatitis, bullous diseases, keloid, erythroderma, drug eruption, and toxicoderma. The pharmaceutical for an inflammatory disease according to the present invention is, for example, a pharmaceutical for an inflammatory skin disease, and also can be referred to as a therapeutic agent, a preventive agent, or an alleviating agent for the disease.

(Method for Inhibiting Immune Cell Activation)

A method for inhibiting immune cell activation according to the present invention includes administering the immune cell activation inhibitor of the present invention to a subject.

The method for inhibiting immune cell activation according to the present invention is characterized in that it includes administering the immune cell activation inhibitor of the present invention, and other configurations are not limited by any means. The immune cell activation inhibitor of the present invention is as described above. The administration conditions of the immune cell activation inhibitor of the present invention are not particularly limited, and may be the same as those described above with regard to the immune cell activation inhibitor of the present invention.

(Method for Protecting Neurons)

A method for protecting neurons according to the present invention includes administering the neuron protective agent of the present invention to a subject. The method for protecting neurons according to the present invention also can be referred to as a method for inhibiting neuron degeneration, for example.

The method for protecting neurons according to the present invention is characterized in that it includes administering the neuron protective agent of the present invention, and other configurations are not limited by any means. The neuron protective agent of the present invention is as described above. The administration conditions of the neuron protective agent of the present invention are not particularly limited, and may be the same as those described above with regard to the immune cell activation inhibitor of the present invention.

(Treatment Method)

A method for treating a neurological disease according to the present invention includes administering the pharmaceutical for a neurological disease according to the present invention to a subject.

The method for treating a neurological disease according to the present invention is characterized in that it includes administering the pharmaceutical for a neurological disease according to the present invention, and other configurations are not limited by any means. The pharmaceutical for a neurological disease according to the present invention is as described above. The administration conditions of the pharmaceutical for a neurological disease according to the present invention are not particularly limited, and may be the same as those described above with regard to the immune cell activation inhibitor of the present invention.

A method for treating an inflammatory disease according to the present invention includes administering the pharmaceutical for an inflammatory disease according to the present invention to a subject.

The method for treating an inflammatory disease according to the present invention is characterized in that it includes administering the pharmaceutical for an inflammatory disease according to the present invention, and other configurations are not limited by any means. The pharmaceutical for an inflammatory disease according to the present invention is as described above. The administration conditions of the pharmaceutical for an inflammatory disease according to the present invention are not particularly limited, and may be the same as those described above with regard to the pharmaceutical for an inflammatory disease according to the present invention.

(Use of Bromovalerylurea or Derivative Thereof)

The present invention relates to: bromovalerylurea or a derivative thereof for inhibiting the immune cell activation; bromovalerylurea or a derivative thereof for protecting neurons or inhibiting the neuron degeneration; bromovalerylurea or a derivative thereof for treating the neurological diseases; and bromovalerylurea or a derivative thereof for treating the inflammatory diseases. Also, the present invention relates to the use of bromovalerylurea or a derivative thereof in production of the above-described various pharmaceuticals.

In the present invention, the term "treatment" encompasses, for example, prevention of diseases, treatment of diseases, and improvement in prognosis of diseases.

EXAMPLES

Next, examples of the present invention will be described. It is to be noted, however, that the present invention is by no means limited by the following examples. Commercially available reagents were used in accordance with their protocols, unless otherwise stated.

Example 1

The present example examined the effect of bromovalerylurea on Parkinson's disease.

(1) Inhibition of Release of Nitric Oxide

As described below, newborn rat-derived primary culture microglia (MG) were cultured in the presence of bromovalerylurea and LPS (lipopolysaccharide), and the amount of nitric oxide, which is a neurocytotoxic factor, released from the MG was measured.

As culture systems, a culture system containing the MG alone and a co-culture system containing the MG and rat-derived primary culture cerebral cortical neurons were provided to carry out culture. The medium used was a serum-free medium (pH 7.4) containing: a Dulbecco's modified Eagle's medium (DMEM) as a basal medium; LPS at a final concentration of 1 μg/ml; and bromovalerylurea at a final concentration of 100 μg/ml. The culture conditions were set to 37° C., 48 hours, and 5% $CO_2$. The concentration of nitrite ions in each of the culture solutions at the end of the culture was measured using a Griess reagent. Because nitric oxide released from the MG was oxidized in the culture solution and turned into nitrite ions, the released nitric oxide was measured indirectly by measuring the nitrite ions.

The results thereof are shown in FIG. 1. FIG. 1 shows graphs showing the nitrite ion concentrations (μmol/L) in the respective culture systems. FIG. 1A shows the result obtained when the culture system containing the MG alone was used. FIG. 1B shows the result obtained when the co-culture system containing the MG and the neurons was used. As can be seen from FIG. 1A, by adding the bromovalerylurea (100 μg/ml), the concentration of the nitrite ions released from the MG was lowered significantly. Normally, when MG are co-cultured with neurons, they are activated strongly and thus release a large amount of nitric oxide. However, as can be seen from FIG. 1B, by adding the bromovalerylurea, the concentration of the released nitrite ions could be inhibited significantly. These results demonstrate that bromovalerylurea can inhibit the release of nitric oxide as a cytotoxic factor from MG.

(2) Inhibition of Transcription of Nitric Oxide Synthase

The present experiment examined whether the inhibition of the release of the nitric oxide described in the item (1) above occurs at the transcription level of nitric oxide synthase (inducible; iNOS) induced by the LPS. Specifically, culture was carried out using a culture system containing MG alone in the same manner as in the item (1), and the amount of transcribed iNOS mRNA was measured by real-time reverse transcription (RT)-PCR. The real-time RT-PCR was carried out by a routine method. Then, assuming that the amount of transcribed iNOS mRNA in a culture system containing no bromovalerylurea was 100%, the relative value (%) of the amount of transcribed iNOS mRNA in the above culture system was determined.

Figure 2:
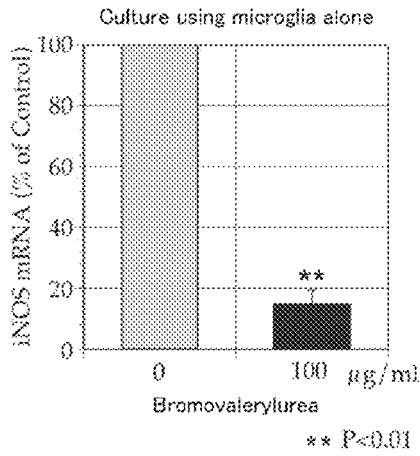
FIG. 2 is a graph showing the amount of mRNA of nitric oxide synthase transcribed in the culture system containing microglia alone in Example 1.

The result thereof is shown in FIG. 2. FIG. 2 is a graph showing the relative value (%) of the amount of the transcribed iNOS mRNA in the culture system. As can be seen from FIG. 2, by adding the bromovalerylurea, the amount of the transcribed iNOS mRNA was decreased significantly. This result demonstrates that inhibition of nitric oxide production by bromovalerylurea occurs at the transcriptional level of iNOS.

(3) MAP2 Expression and Inhibition of iNOS Expression

Regarding each of the culture system containing the MG alone and the co-culture system containing the MG and the neurons, the expression of a neuron-specific protein MAP2 and the expression of an iNOS protein producing nitric oxide were measured.

Culture was carried out in the same manner as in the item (1) above. Then, by Western blotting using an antibody against mouse-derived MAP2 (trade name: Mouse monoclonal anti-MAP2 antibody (clone AP20), commercially available from Sternberger Monoclonals) and an antibody against mouse-derived iNOS (trade name: Mouse monoclonal anti-iNOS antibody (clone 6), commercially available from BD Biosciences), the MAP2 immunoreactivity and the iNOS immunoreactivity corresponding to the expression levels of the proteins were measured. Then, assuming that the MAP2 immunoreactivity and the iNOS immunoreactivity in a culture system containing no bromovalerylurea were 100%, the relative value (%) of each immunoreactivity in each culture system was determined.

Figure 3:
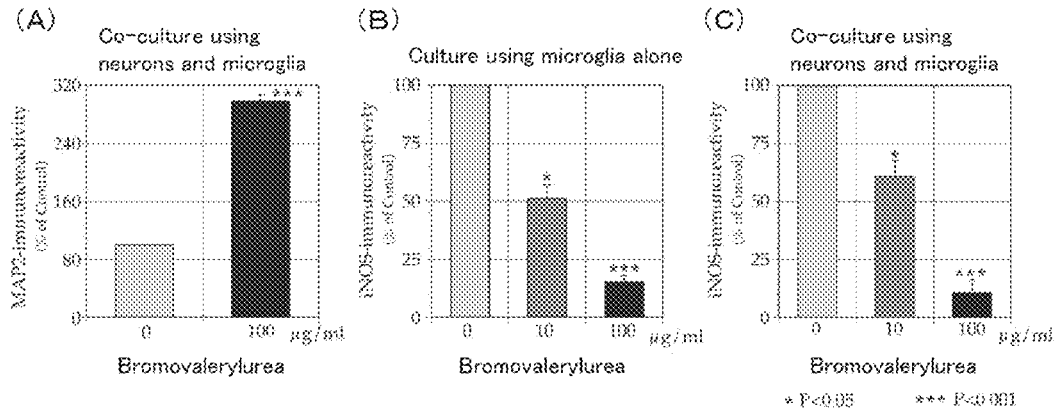
FIG. 3A is a graph showing the expression level of MAP2 in the co-culture system containing neurons and microglia in Example 1.
FIG. 3B is a graph showing the expression level of nitric oxide synthase in the culture system containing microglia alone in Example 1.
FIG. 3C is a graph showing the expression level of nitric oxide synthase in the co-culture system containing neurons and microglia in Example 1.

The results thereof are shown in FIG. 3. FIG. 3A is a graph showing the MAP2 immunoreactivity in the co-culture system. FIG. 3B is a graph showing the iNOS immunoreactivity in the culture system containing the MG alone. FIG. 3C is a graph showing the iNOS immunoreactivity in the co-culture system. As can be seen from FIG. 3A, by adding the bromovalerylurea, the expression level of the neuron-specific protein MAP2 was increased greatly as compared with the case where bromovalerylurea was not added. This result demonstrates that neuron death was inhibited in the co-culture system. Also, as can be seen from FIGS. 3B and 3C, by adding the bromovalerylurea, the expression level of the iNOS was decreased in a bromovalerylurea concentration dependent manner. These results demonstrate that bromovalerylurea can inhibit the expression of iNOS induced by LPS and thus can inhibit neuron death.

(4) Inhibition of Death of Dopamine Neurons in Parkinson's Disease Model Rats

The present experiment examined whether bromovalerylurea inhibits neuron death in rat Parkinson's disease models in which the Parkinson's disease was induced by 6-hydroxydopamine (6-OHDA).

The model rats used were those having dopamine neuron injury in the substantia nigra on the right side of the midbrain, induced by injecting 6-OHDA to the right striatum (see Choudhury et al., Brain and Behavior, 1: pp. 26-43, 2011). To the model rats (n=5), drinking water containing 500 mg/l bromovalerylurea was administered orally for 7 days in such a manner that each rat drank an average of 25 ml of the drinking water per day. Then, on the last day of the oral administration, each model rat was dissected, and the substantiae nigra on the right and left sides of the midbrain were collected. Then, the thus-collected midbrain substantiae nigra were subjected to immunoblot to measure tyrosine hydroxylase (TH) as a dopamine neuron marker. Also, as a control, TH was measured in the same manner, except that drinking water not containing bromovalerylurea was used instead of the drinking water containing bromovalerylurea. Then, regarding each rat group, the ratio (%) of the TH immunoreactivity (R) in the substantia nigra on the right side of the midbrain where the injury was induced to the TH immunoreactivity (L) in the substantia nigra on the left side of the midbrain where injury was not induced was calculated according to the following equation.

$$\text{Relative value (\%)} = 100 \times R/L$$

Furthermore, the model rats to which the bromovalerylurea had been administered orally for 7 days were reared for further 3 days. Thereafter, the motor function of each model rat was measured by a rotarod test.

Figure 4:
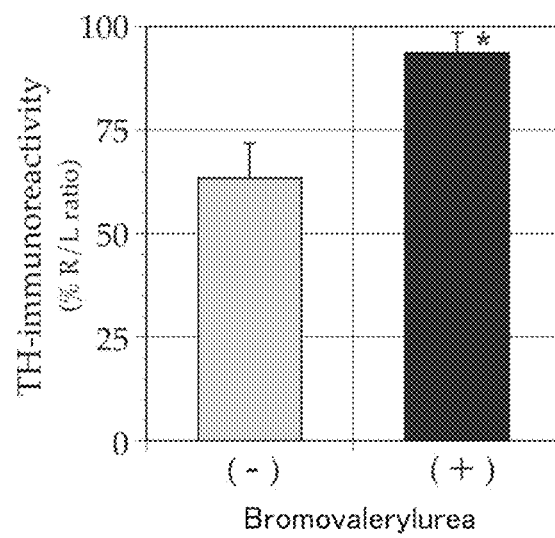
FIG. 4A is a graph showing the expression level of tyrosine hydroxylase in model rats in Example 1.
FIG. 4B is a graph showing the total number of revolutions of a rotating rod until the model rat fell from the rotating rod in Example 1.
Figure 4:
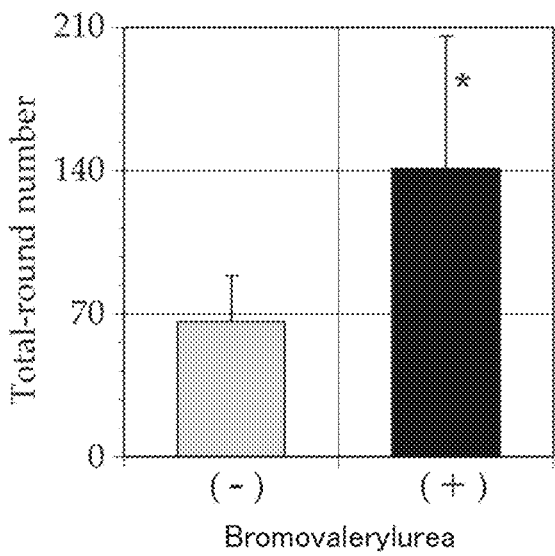

The results thereof are shown in FIG. 4. FIG. 4A is a graph showing the TH immunoreactivity. As can be seen from FIG. 4A, in the control where the bromovalerylurea had not been administered, the TH immunoreactivity in the substantia nigra on the right side of the midbrain was deteriorated greatly, whereas, in the example where the bromovalerylurea had been administered, the deterioration of the TH immunoreactivity in the substantia nigra on the right side of the midbrain was inhibited sufficiently. These results demonstrate that bromovalerylurea can inhibit the death of dopamine neurons in the midbrain substantia nigra. FIG. 4B is a graph showing the results of the rotarod test. FIG. 4B shows the total number of revolutions of a rotating rod until the model rat fell from the rotating rod. The model rats to which the bromovalerylurea had been administered could stay on the rotating rod longer than the model rats to which the bromovalerylurea had not been administered. This result demonstrates that bromovalerylurea can inhibit the movement disorder in Parkinson's disease.

Example 2

The present example examined the effect of bromovalerylurea on cerebral infarction.

(1) Inhibition of Tissue Loss in Cerebral Infarction Model Rats

Cerebral infarction model rats each having cerebral infarction induced by 90-minute transient occlusion of the right middle cerebral artery were used to examine whether bromovalerylurea inhibits tissue loss.

As the model rats, male Wistar rats were used (Matsumoto et al., Journal of Cerebral Blood Flow & Metabolism (2008) 28: pp. 149-163). By magnetic resonance imaging (MRI), only the model rats in which cerebral infarction had been induced sufficiently were selected (n=4). To these model rats, drinking water containing 500 mg/l bromovalerylurea was administered orally for 14 days in such a manner that each rat drank an average of 25 ml of the drinking water per day. On Day 16 from the last day of oral administration, each model rat was dissected, and a middle cerebral artery perfusion region in the brain was collected. The collected perfusion region was sliced from the anterior side to the posterior side so as to provide seven layers of slices. Then, regarding the 2nd, 3rd, and 4th layers from the top, the total volume of the left hemisphere where infarction was not caused and the total volume of the right hemisphere where infarction was caused were measured separately, and the mean values were determined (L: the total volume of the left hemisphere, R: the total volume of the right hemisphere). Then, the proportion of the tissue loss (%) was calculated according to the following equation.

$$\text{Proportion of tissue loss (\%)}=100\times(L-R)/L$$

Figure 5:
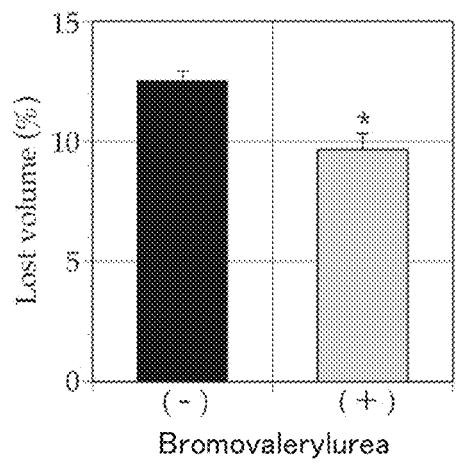
FIG. 5 is a graph showing the proportion of brain tissue loss in model rats in Example 2.

The results thereof are shown in FIG. 5. FIG. 5 is a graph showing the proportion of the brain tissue loss. As can be seen from FIG. 5, in the example where the bromovalerylurea had been administered, the proportion of the brain tissue loss could be lowered as compared with the control where the bromovalerylurea had not been administered. These results demonstrate that bromovalerylurea can inhibit the brain tissue loss in cerebral infarction.

(2) Inhibition of iNOS Expression and Inhibition of Nitric Oxide Production

The present experiment examined whether bromovalerylurea inhibits iNOS expression and nitric oxide production in macrophages BINCs accumulated in a cerebral infarction nest. Regarding the BINCs, Matsumoto et al., Journal of Cerebral Blood Flow & Metabolism (2008) 28: pp. 149-163 was referenced to.

Culture was carried out using, as the macrophages, primary culture brain macrophages (BINCs) derived from the core lesion of rat cerebral infarction caused by transient occlusion of the middle cerebral artery. The medium used was a serum-free medium (pH 7.4) containing: the DMEM as a basal medium; and bromovalerylurea at a final concentration of 0 or 100 µg/ml. The culture conditions were set to 37° C., 24 hours, and 5% $CO_2$. Nitrite ions in the culture solution at the end of the culture were measured. Also, iNOS and β-actin were measured by immunoblot, and the ratio between the immunoreactivities of iNOS and β-actin (iNOS/β-actin) was calculated. Then, assuming that the ratio when the culture system not containing bromovalerylurea was used was 100%, the relative value (%) of the ratio when the above culture system was used was determined.

Figure 6:
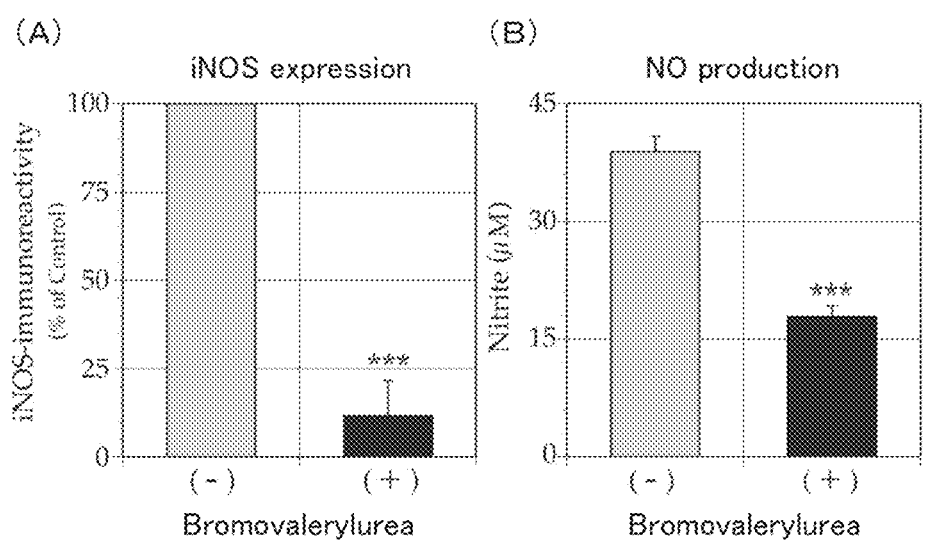
FIG. 6A is a graph showing the expression level of nitric oxide synthase in culture systems in Example 2.
FIG. 6B is a graph showing the amount of nitric oxide produced in the culture systems.

The results thereof are shown in FIG. 6. FIG. 6A is a graph showing the iNOS immunoreactivity. FIG. 6B is a graph showing the concentration of nitrite ions. As can be seen from FIG. 6A, by adding the bromovalerylurea, the expression level of iNOS was lowered. Also, as can be seen from FIG. 6B, by adding the bromovalerylurea, the amount of the produced nitrite ions, i.e., the amount of the produced nitric oxide, was decreased. These results demonstrate that bromovalerylurea can inhibit the iNOS expression in macrophages BINCs accumulated in a cerebral infarction core lesion and thus can inhibit the production of nitric oxide.

(3) Inhibition of Inflammatory Reaction

The present experiment examined whether bromovalerylurea inhibits an inflammatory reaction in macrophages BINCs accumulated in a cerebral infarction core lesion.

Macrophages were cultured in the same manner as in the item (2) above. Then, the amounts of transcribed mRNAs of various factors in the medium after the end of the culture were measured by RT-PCR. Then, assuming that the amounts of the mRNAs transcribed in a culture system not containing bromovalerylurea were 100%, the relative values (%) of the amounts of the mRNAs transcribed in each culture system were determined.

Figure 7:
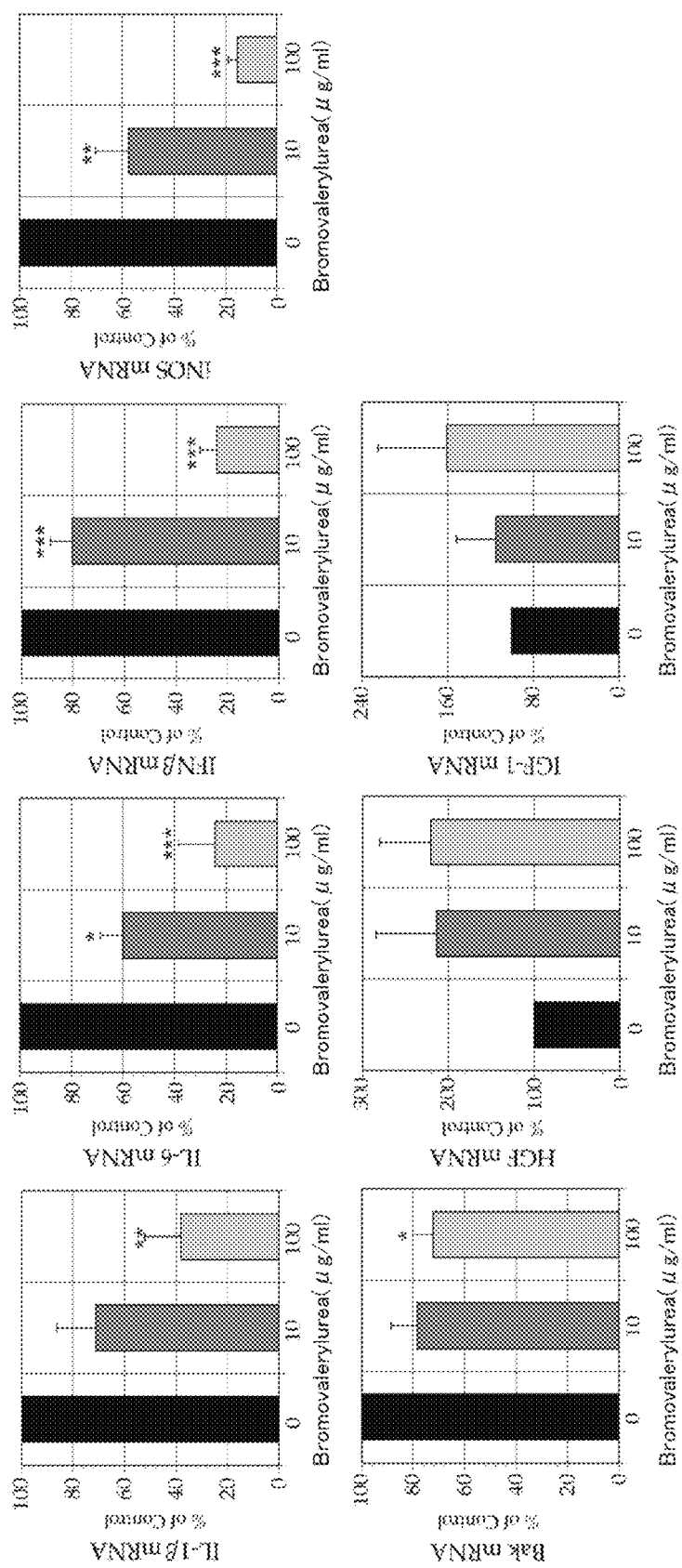
FIG. 7 shows graphs showing the amounts of mRNAs of various factors transcribed in culture systems in Example 2.

The results thereof are shown in FIG. 7. FIG. 7 shows graphs showing the amounts of the transcribed mRNAs of the various factors. As can be seen from FIG. 7, the amounts of the transcribed mRNAs of neurocytotoxic factors IL-1β, IL-6, IFNβ, and Bak and the amount of the transcribed mRNA of the iNOS, which is an enzyme that produces nitric oxide as a neurocytotoxic factor, were decreased in a bromovalerylurea concentration dependent manner. In contrast, the amounts of the transcribed mRNAs of HGF and IGF-1, which are factors useful for cell growth, were not decreased by the addition of the bromovalerylurea and were not influenced by the bromovalerylurea.

(4) Inhibition of Brain Tissue Loss Caused by Needlestick Injury

Brain injury model rats each having brain injury caused by inserting an injection needle from the outside of the cranium were used to examine whether bromovalerylurea inhibits tissue loss.

As the rats, male Wistar rats were used. In each rat, a needle (18-gauge injection needle) was inserted into the cerebrum at a site 2 mm posterior and 2 mm lateral to the right from the anterior fontanelle, and a fan-shaped injury extending in an anteroposterior direction and having an angle of about 120° was formed. To the rats (n=5), drinking water containing 500 mg/l bromovalerylurea was administered orally for 60 days in such a manner that each rat drank an average of 25 ml of the drinking water per day. Then, on Day 3 from the last day of oral administration, each model rat was dissected, and the cerebrum was collected. The collected cerebrum was sliced from the anterior side to the posterior side so as to provide seven layers of slices. Then, regarding the 2nd to 5th layers from the top, the volume of the left hemisphere and the volume of the right hemisphere were measured separately, and the mean values were determined (L: the volume of the left hemisphere, R: the volume of the right hemisphere). As a control experiment, drinking water not containing bromovalerylurea was administered orally to rats having brain injury caused in the same manner, and the volumes of the right and left hemispheres of the brain were measured in the same manner. Then, the proportion of tissue loss (%) was calculated according to the following equation.

$$\text{Proportion of tissue loss (\%)}=100\times(L-R)/L$$

Figure 8:
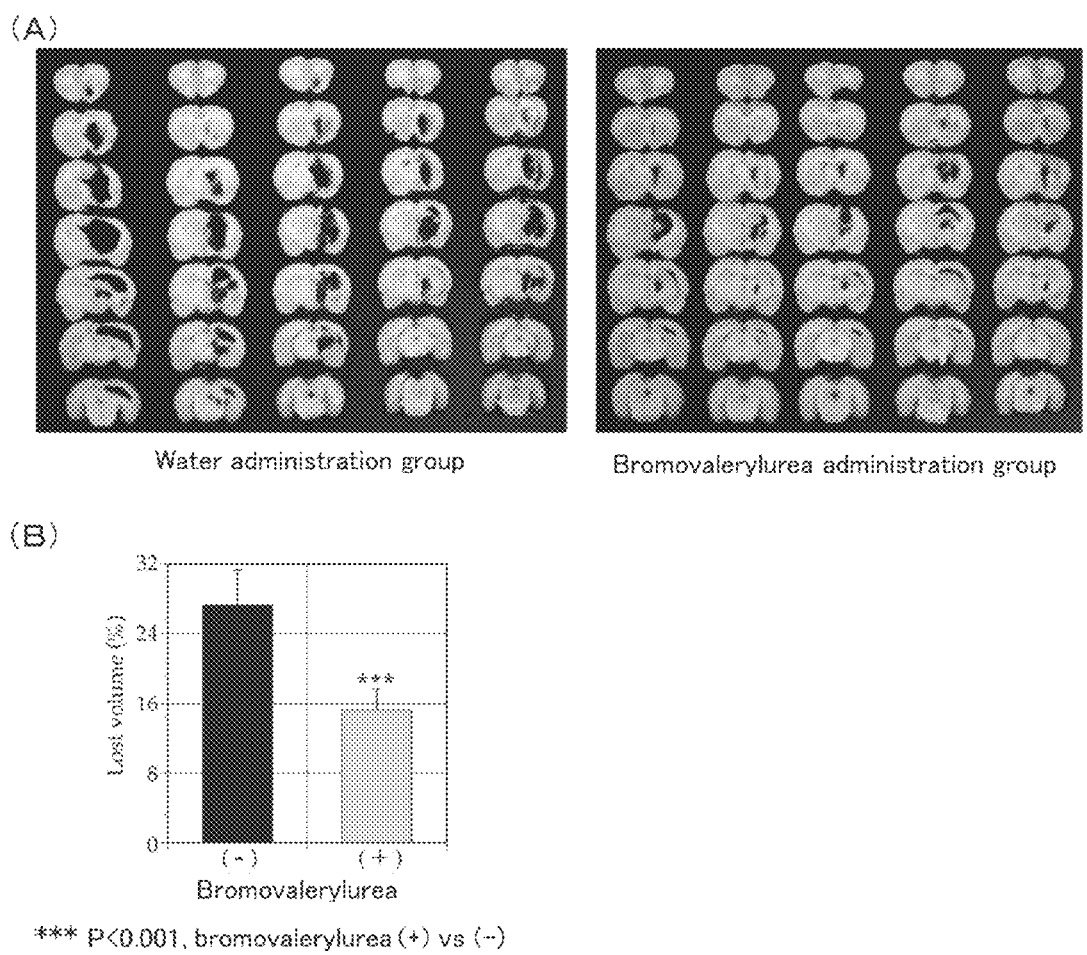
FIG. 8A shows photographs showing cross sections of the brains of rats having brain injury in Example 2.
FIG. 8B is a graph showing the proportion of brain tissue loss in the rats having brain injury.

The results thereof are shown in FIG. 8. FIG. 8A shows photographs showing the brain tissue loss. The photograph on the left shows the results obtained regarding the group to which the drinking water not containing bromovalerylurea had been administered, and the photograph on the right shows the results obtained regarding the group to which the drinking water containing bromovalerylurea had been administered. As can be seen from FIG. 8A, considerable brain tissue loss was seen in the group to which bromovalerylurea had not been administered, whereas the brain tissue loss was inhibited in the group to which the bromovalerylurea had been administered. FIG. 8B is a graph showing the proportion of the brain tissue loss. As can be seen from FIG. 8B, the proportion of the brain tissue loss in the group to which the bromovalerylurea had been administered (+) could be lowered as compared with that in the group to which bromovalerylurea had not been administered (−). These results demonstrate that bromovalerylurea can inhibit brain tissue loss caused by brain injury.

Example 3

The present example examined the effect of bromovalerylurea on sepsis.

(1) Effect of Improving Survival Rate

The cecum of each of 8-week old male Wistar rats was ligated, and two perforations were formed with an 18-gauge injection needle in the ligated part of the cecum. Thus, perforative peritonitis was caused to prepare rat sepsis models. Immediately after the preparation of the model rats, 10 ml of a commercially available maintenance infusion solution (SOLITA T3, Ajinomoto Pharmaceuticals Co., Ltd.) in which bromovalerylurea had been dissolved at a final concentration of 500 µg/ml was injected subcutaneously to the model rats. As a control group, the same amount of the maintenance infusion solution not containing bromovalerylurea was injected subcutaneously. Thereafter, the injection was performed in the same manner about every 12 hours. Also, rats subjected only to laparotomy, i.e., the incision of the skin and the peritoneum with no injury to the intestinal tract, were provided as a sham operation group. To the sham operation group, subcutaneous injection was not performed. The results obtained regarding the model rats of the respective groups were examined over 8 days after the incision.

Figure 9:
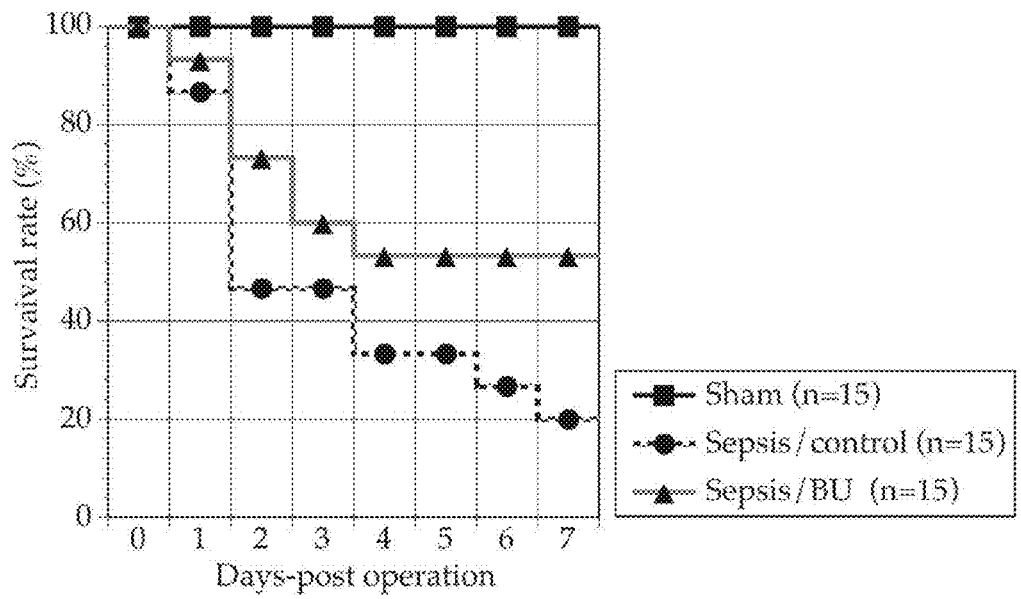
FIG. 9 is a graph showing the survival rate in Example 3.

The results thereof are shown in FIG. 9. In FIG. 9, the filled square (■) shows the results obtained regarding the sham operation group, the filled circle (●) shows the results obtained regarding the control group to which bromovalerylurea had not been administered, and the filled triangle (▲) shows the results obtained regarding the example group to which the bromovalerylurea had been administered. As can be seen from FIG. 9, in the sham operation group (Sham), the mortality rate was 0%. In the group to which bromovalerylurea had not been administered (Sepsis/control), the mortality rate was 80% on Day 8. In contrast, in the example group to which the bromovalerylurea had been administered (Sepsis/BU), the mortality rate could be lowered to 47% with the significant difference of $P<0.0001$. These results demonstrate that bromovalerylurea exhibits significant lifesaving effect.

(2) Inhibition of Production of Proinflammatory Interleukins

The present experiment examined whether bromovalerylurea inhibits the production of interleukins induced by peritoneal macrophages.

Culture was carried out using, as macrophages, macrophages collected in the abdominal cavities of Wistar rats. The medium used was a serum-free medium (pH 7.4) containing: the DMEM as a basal medium; and bromovalerylurea at a final concentration of 0, 30, or 100 µg/ml. The culture conditions were set to 37° C., 18 hours, and 5% $CO_2$. The concentrations of IL-6 and IL-1β in each culture solution at the end of the culture were measured by ELISA.

Figure 10:
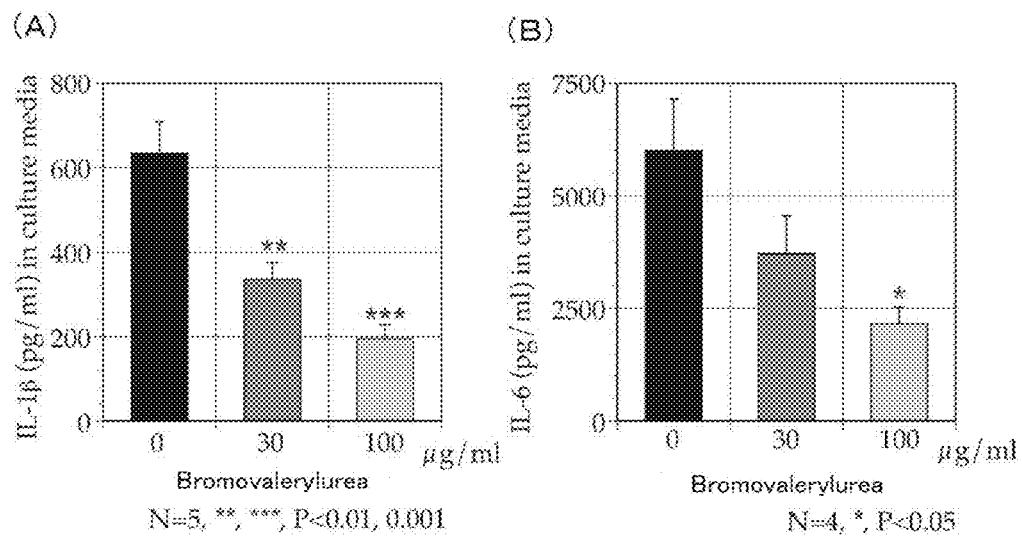
FIG. 10A is a graph showing the amount of IL-1β produced in culture systems in Example 3.
FIG. 10B is a graph showing the amount of IL-6 produced in the culture systems.

The results thereof are shown in FIG. 10. FIG. 10A is a graph showing the amount of the produced IL-1β. FIG. 10B is a graph showing the amount of the produced IL-6. As can be seen from FIGS. 10A and 10B, by adding the bromovalerylurea, the amounts of the produced IL-6 and IL-1β were decreased in a bromovalerylurea concentration dependent manner. These results demonstrate that bromovalerylurea can inhibit inflammation.

(3) Inhibition of IL-6 and Inhibition of Renal Failure in Sepsis Model Rats

Sepsis model rats were used to examine whether bromovalerylurea inhibits IL-6.

The sepsis model rats were prepared by ligating the cecum of each of male Wistar rats and then forming two perforations with an 18-gauge injection needle. To the model rats (n=10), a commercially available maintenance infusion solution (SOLITA T3, Ajinomoto Pharmaceuticals Co., Ltd.) in which bromovalerylurea had been dissolved at a final concentration of 500 µg/ml was injected subcutaneously three times in total for about one day, in such a manner that the subcutaneous injection was performed twice a day (once before noon and once in the afternoon) with the single dose being 10 ml and the total dose per day being 20 ml. After the third subcutaneous injection, i.e., on the following day of the preparation of the sepsis model by causing perforative peritonitis, serum of each model rat was collected, and serum IL-6 was measured by ELISA. As a comparative example, the maintenance infusion solution not containing bromovalerylurea was injected subcutaneously to the sepsis rats, and serum IL-6 was measured in the same manner. Also, as a control, regarding non-sepsis rats subjected only to laparotomy (sham operation group), serum IL-6 was measured in the same manner. Furthermore, regarding each serum, the creatinine concentration in serum as a renal failure indicator also was measured.

Figure 11:
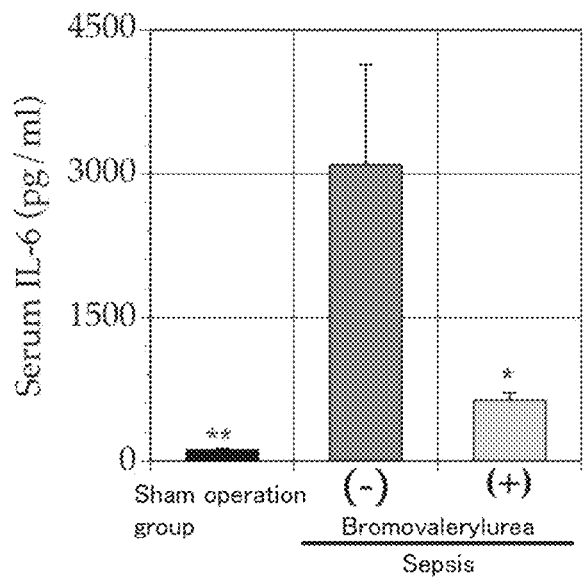
FIG. 11A is a graph showing the amount of serum IL-6 produced in sepsis model rats in Example 3.
FIG. 11B is a graph showing the amount of serum creatinine in the sepsis model rats.
Figure 11:
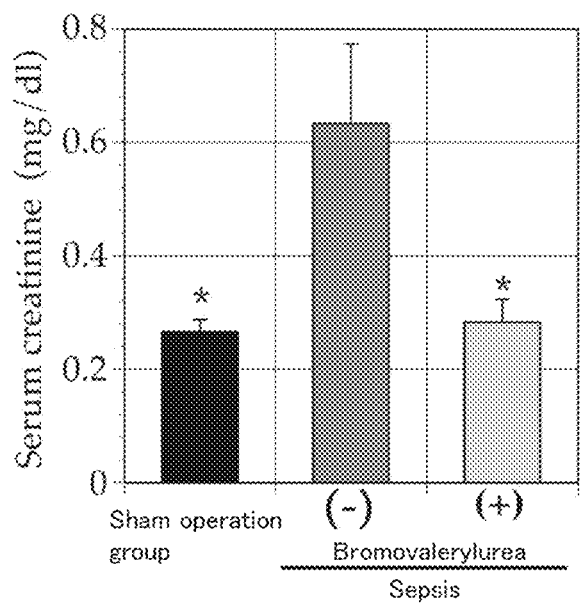

The results thereof are shown in FIG. 11. FIG. 11A is a graph showing serum IL-6. As can be seen from FIG. 11, in the example where the bromovalerylurea had been administered, serum IL-6 could be decreased greatly as compared with the comparative example (−) where bromovalerylurea had not been administered. This result demonstrates that bromovalerylurea can inhibit cytokine storm in sepsis.

FIG. 11B is a graph showing the creatinine concentration in serum. In the comparative example (−) where bromovalerylurea had not been administered, the creatinine concentration increased significantly, resulting in renal failure. In contrast, in the example (+) where the bromovalerylurea had been administered, by the subcutaneous injection of the bromovalerylurea, the creatinine concentration was restored to a substantially normal level. It can be said that these results demonstrate that bromovalerylurea can greatly inhibit the onset of renal failure or multiple organ failure induced by sepsis.

(4) Inhibition of Inflammation in Sepsis Model Rats

Sepsis model rats were used to examine whether bromovalerylurea inhibits swelling and inflammation of the small intestine.

To the same sepsis model rats as those used in the item (3) above, a commercially available maintenance infusion solution (SOLITA T3, Ajinomoto Pharmaceuticals Co., Ltd.) in which bromovalerylurea had been dissolved at a final concentration of 500 µg/ml was administered by subcutaneous injection twice a day. Then, on the following day of the preparation of the sepsis model, the abdomen of each model rat was opened to examine the small intestine (sepsis/treated group). Also, the same procedure was carried out with respect to sepsis models to which the maintenance infusion solution not containing bromovalerylurea had been injected subcutaneously (sepsis/untreated group) and to non-sepsis rats subjected to laparotomy only (sham operation group).

Figure 12:
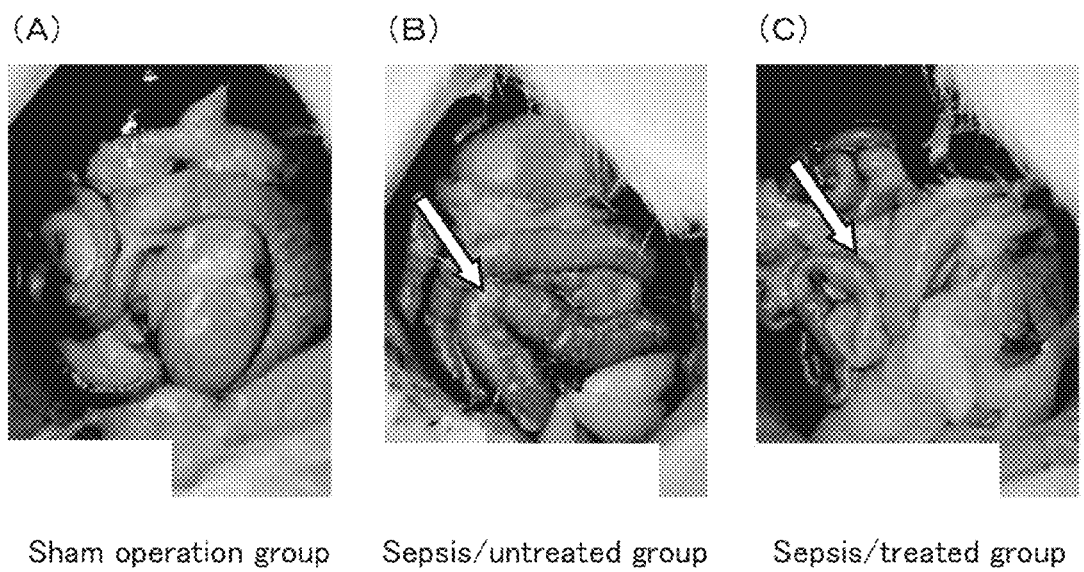
FIGS. 12A to 12C are photographs showing the small intestines of the sepsis model rats in Example 3.

The results thereof are shown in FIG. 12. FIG. 12 shows photographs of the small intestines. FIG. 12A shows the small intestine of the rat in the sham operation group. FIG. 12B shows the small intestine of the rat in the sepsis/untreated group. FIG. 12C shows the small intestine of the rat in the sepsis/treated group. In FIG. 12B, in the sepsis/untreated group to which bromovalerylurea had not been administered, swelling of the small intestine was caused, as indicated with the arrow. In contrast, in FIG. 12C, in the sepsis/treated group to which bromovalerylurea had been administered, the swelling of the small intestine was inhibited greatly as indicated with the arrow, and the result shown in FIG. 12C was similar to the result regarding the sham operation group shown in FIG. 12A.

Figure 13:
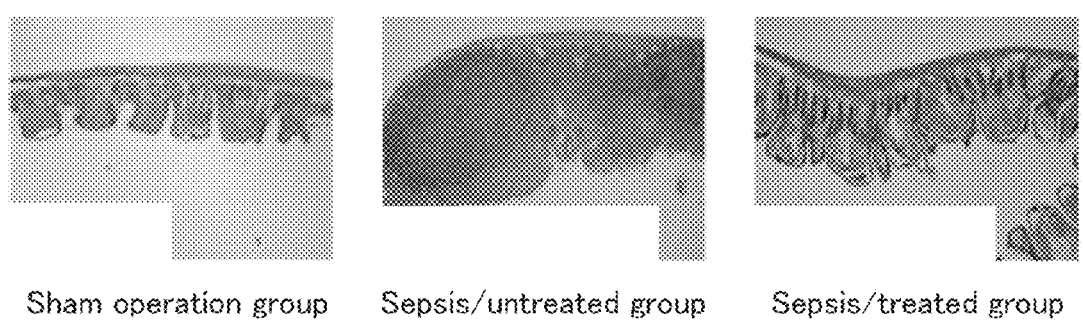
FIGS. 13A to 13C are micrographs showing the small intestines of the sepsis model rats in Example 3.

Micrographs of the small intestines of the respective groups also are shown in FIG. 13. FIG. 13A shows the result obtained regarding the sham operation group. FIG. 13B shows the result obtained regarding the sepsis/untreated group. FIG. 13C shows the result obtained regarding the sepsis/treated group. As can be seen from FIG. 13B, it is interpreted that the swelling of this small intestine was caused by a high level of accumulation of lymphocytes, macrophages, and leukocytes such as neutrophils. These results demonstrate that, for example, bromovalerylurea can inhibit reactive hyperplasia of lymphatic tissues in the small intestine and thus can inhibit inflammation.

(5) Inhibition of iNOS Induction and Interleukin Production

The present experiment examined whether bromovalerylurea inhibits iNOS induction and interleukin production induced by alveolar macrophages.

Culture was carried out using, as macrophages, macrophages derived from the pulmonary alveoli of Wistar rats. The medium used was a serum-free medium (pH 7.4) containing: the DMEM as a basal medium; and bromovalerylurea at a final concentration of 0, 30, or 100 μg/ml. The culture conditions were set to 37° C., 18 hours, and 5% $CO_2$. Then, at the end of the culture, total RNA of the alveolar macrophage was collected. Then, the amounts of transcribed mRNAs encoding iNOS, IL-6, and IL-1β were measured by quantitative real-time RT-PCR. Then, assuming that the measured values in the culture system not containing bromovalerylurea were 100%, the relative values (%) of the measured values in each culture system were determined.

Figure 14:
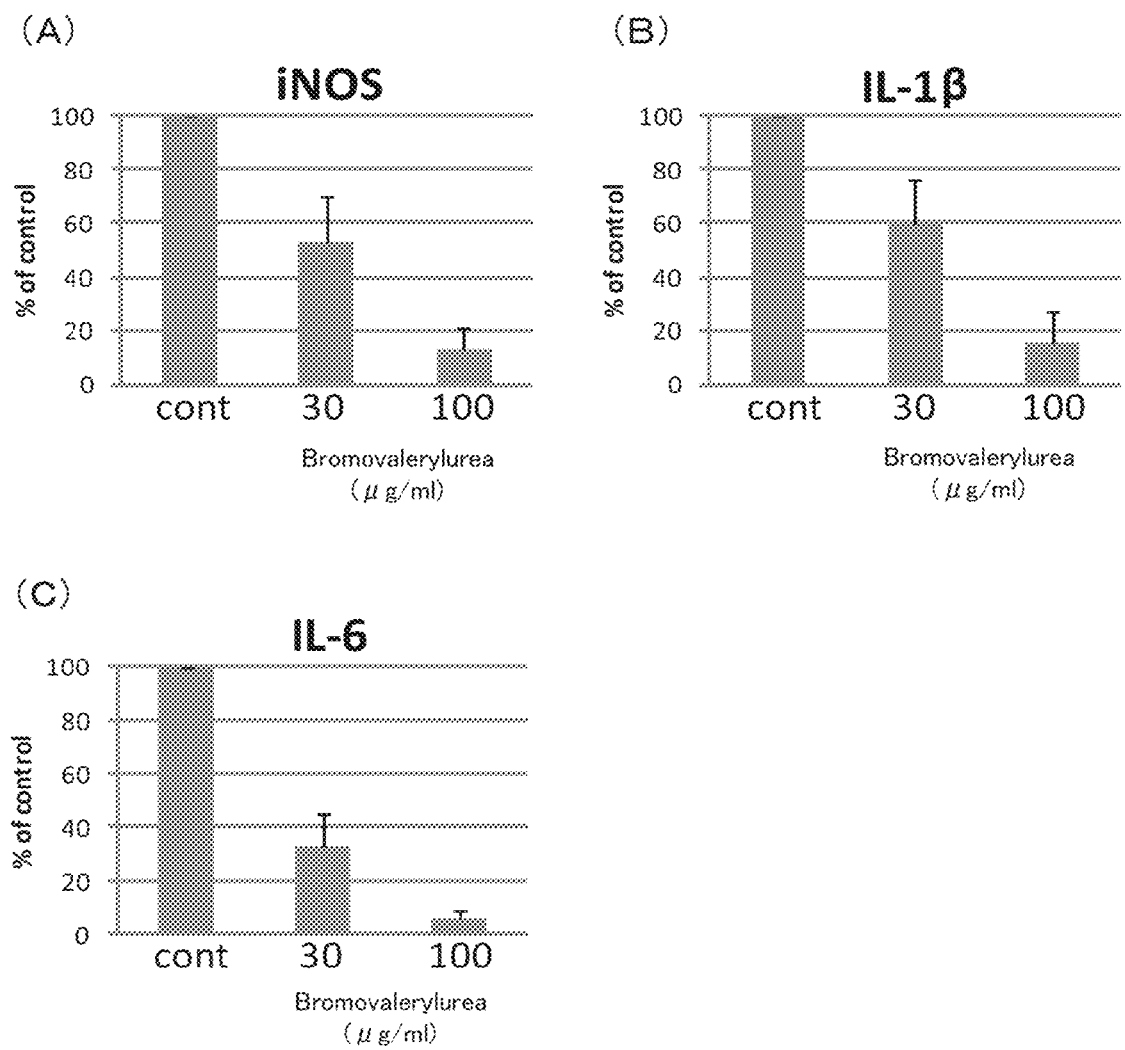
FIG. 14A is a graph showing the expression level of nitric oxide synthase.
FIG. 14B is a graph showing the amount of produced IL-1β.
FIG. 14C is a graph showing the amount of produced IL-6.

The results thereof are shown in FIG. 14. FIG. 14A shows the relative value regarding iNOS. FIG. 14B shows the relative value regarding IL-1β. FIG. 14C shows the relative value regarding IL-6. As can be seen from FIG. 14, by adding the bromovalerylurea, the amounts of the transcribed mRNAs of iNOS, IL-1β, and IL-6 were decreased in a bromovalerylurea concentration dependent manner. These results demonstrate that bromovalerylurea can inhibit inflammation. Moreover, because bromovalerylurea also can inhibit the expression of inflammatory cytokines caused by alveolar macrophages, it is considered that bromovalerylurea also can inhibit ARDS and the like associated with sepsis, for example.

Example 4

The present example examined the effect of bromovalerylurea on inflammation in an inflammatory skin disease.

(1) Inhibition of Inflammation in Contact Dermatitis Caused by Rubber of Underwear A bromovalerylurea ointment (BU ointment) was prepared by dissolving bromovalerylurea in a Hirudoid Soft Ointment 0.3% (Maruho Co., Ltd.) so that the concentration thereof became 1% (w/w). The subject was a patient with an inflammatory skin disease. The primary lesion of the inflammatory skin disease was contact dermatitis caused by the rubber of underwear when wearing the underwear, which was then developed into autosensitization dermatitis. To an inflammation part (about 25 $cm^2$) including papules in the abdominal region of the patient, 0.5 g of the BU ointment was applied. The abdominal region was observed immediately before the application of the BU ointment, 25 minutes after the application, and 3 hours after the application. To the inflammation region of the same patient, the BU ointment further was applied twice a day for 10 days. Then, the abdominal region was observed in the same manner on Day 10 from the start of the application and Day 10 after the stop of the application (Day 20 from the start of the application).

Figure 15:
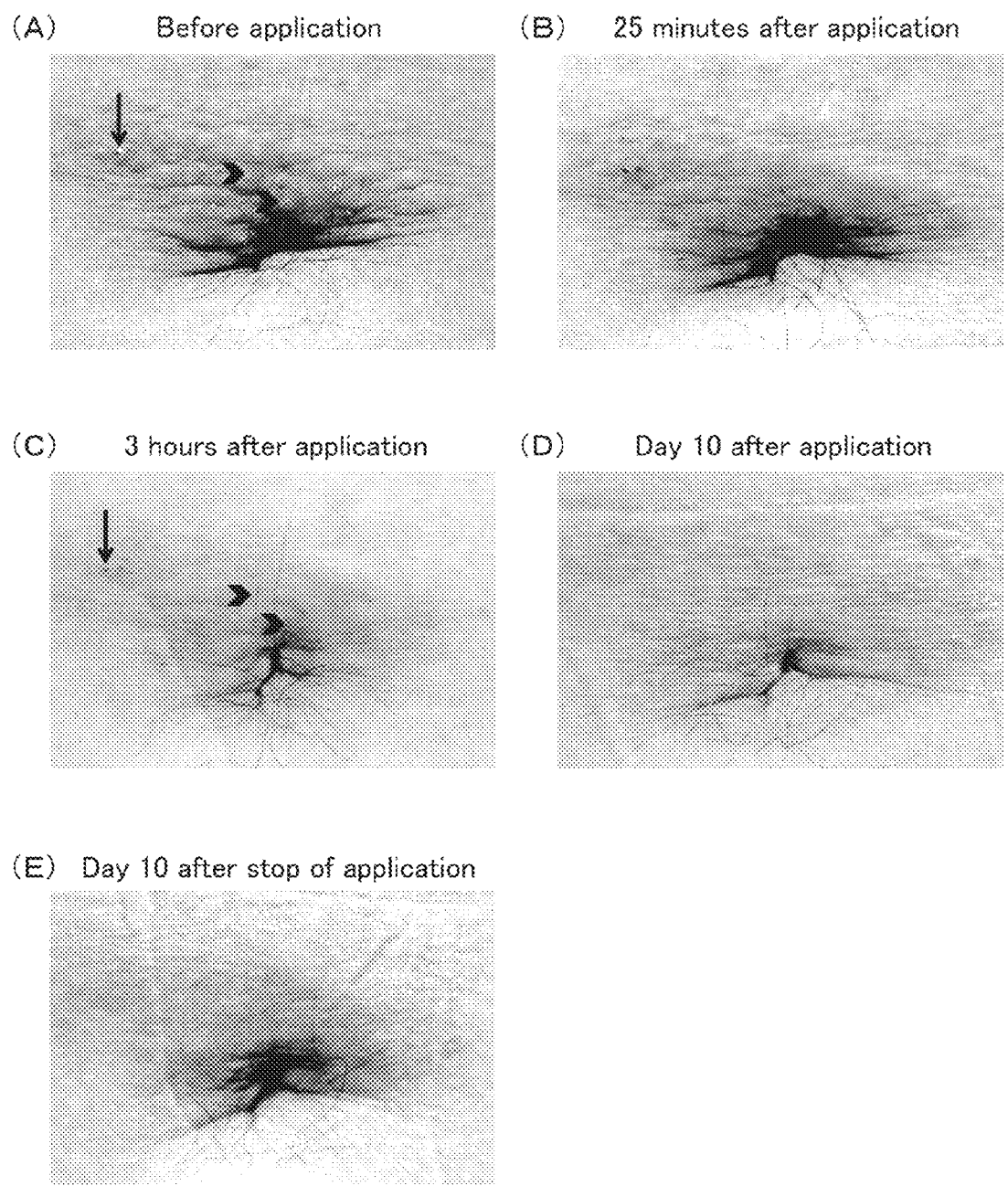
FIGS. 15A to 15E are photographs each showing the abdominal region of a patient with an inflammatory skin disease in Example 4.

The results thereof are shown in FIG. 15. FIG. 15 shows photographs each showing the abdominal region of the patient. FIG. 15A shows the state before the application, FIG. 15B shows the state 25 minutes after the application, FIG. 15C shows the state 3 hours after the application, FIG. 15D shows the state on Day 10 from the start of the application, and FIG. 15E shows the state on Day 10 after the stop of the application.

Before the application of the BU ointment, the patient had strong itching sensation in the inflammation part of the abdominal region. As can be seen from FIG. 15A, in the abdominal region of the patient, many papules (elevation of the skin with a diameter of 1 cm or less) were formed, and on the papules, excoriations (indicated with the arrowhead figures in FIG. 15A) and a newly-formed red erosion (indicated with the arrow in FIG. 15A) were observed. Around 15 minutes after the application, the patient was relieved of the itching sensation in the inflammation part of the abdominal region. 25 minutes after the application, the papules seen in FIG. 15A began to disappear, as can be seen from FIG. 15B. Furthermore, 3 hours after the application, the patient became free of the itching sensation in the inflammation part of the abdominal region. Further, as can be seen from FIG. 15C, the disappearance of the papules became more noticeable, the red color of the erosion seen in FIG. 15A faded (the arrow in FIG. 15C), and the excoriations on the papules became less conspicuous than those in FIG. 15A (indicated with the arrowhead figures in FIG. 15C). Then, on Day 10 from the start of the application, the patient no longer had any subjective symptom, although the redness of the abdominal region remained slightly, and papules were no longer observed as can be seen from FIG. 15D. Moreover, on Day 10 after the stop of the application, no papules were formed as can be seen from FIG. 15E, and the recurrence of inflammation was not observed. These results demonstrate that bromovalerylurea can inhibit inflammation in contact dermatitis and can treat the inflammatory skin disease.

(2) Inhibition of Inflammation in Contact Dermatitis Caused by Rubber of Stockings The subject was a patient who had contact dermatitis caused by the rubber of stockings when wearing the stockings on the inside of the respective knees. To a linear wheal (about 20 $cm^2$) on the inside of the left knee of the patient, 0.4 g of the BU ointment prepared in the above item (1) was applied. The inside of the left knee was observed immediately before the application of the BU ointment and 35 minutes after the application. Also, as a control, the inside of the right knee of the same patient was observed in the same manner, except that a Hirudoid Soft Ointment 0.3% (control ointment) containing no bromovalerylurea was applied to a linear wheal on the inside of the right knee of the patient.

Figure 16:
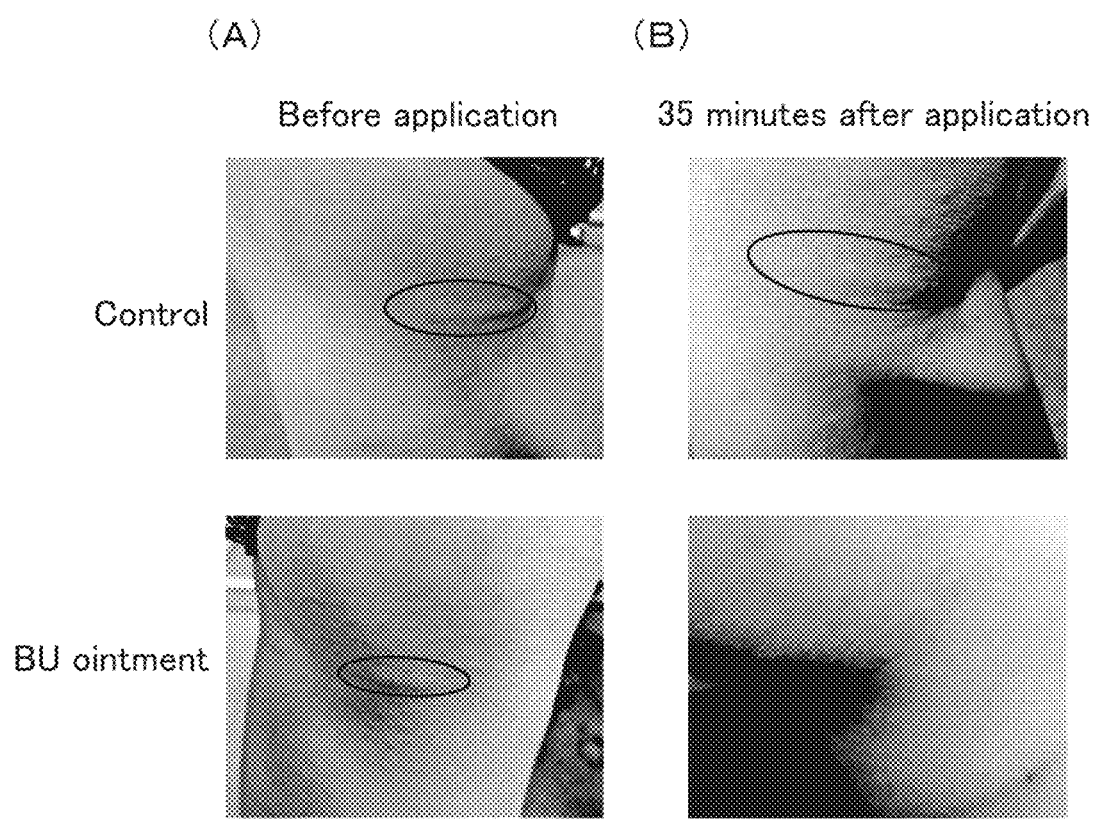
FIGS. 16A and 16B each show photographs of the skins on the inside of the respective knees of a patient with an inflammatory skin disease in Example 4.

The results thereof are shown in FIG. 16. FIG. 16 shows photographs of the inside of the respective knees of the patient. FIG. 16A are photographs showing the states before the application, and FIG. 16B are photographs showing the states 35 minutes after the application. In each of FIGS. 16A and 16B, the upper row shows the result obtained when the control ointment was used, and the lower row shows the result obtained when the BU ointment was used.

Before the application of the BU ointment or the control ointment, as can be seen from FIG. 16A, on the skins on the inside of the respective knees of the patient, erythema and linear wheals were formed substantially symmetrically (regions enclosed with the solid line in the upper and lower photographs in FIG. 16A), which were accompanied with itches. In the right knee to which the control ointment had been applied, no change was seen in the erythema and the wheal even 35 minutes after the application (the region enclosed with the solid line in the upper photograph in FIG. 16B), as can be seen from the upper row in FIG. 16B, and the itching still remained. In contrast, in the left knee to which the BU ointment had been applied, the erythema disappeared and the wheal mostly disappeared 35 minutes after the application, as can be seen from the lower row in FIG. 16B, and also, the itching was gone. These results demonstrate that bromovalerylurea can inhibit inflammation in contact dermatitis and can treat the inflammatory skin disease.

(3) Inhibition of Inflammation in Atopic Dermatitis Model Mice

Murine atopic dermatitis model mice were used to examine whether bromovalerylurea inhibits inflammation in atopic dermatitis.

To the skin in a dorsal region of each of 8-week old NC/Nga female mice (n=6), a mite body component-containing ointment (Biostir AD, Biostir Inc.) was applied to induce atopic dermatitis. The ointment was applied twice a week for three weeks in accordance with its instructions for use. Next, to the skin in the dorsal region (about 7 cm$^2$) of each of the model mice (n=3) having the induced atopic dermatitis, 0.1 g of the BU ointment was applied. The skin in the dorsal region was observed immediately before the application of the BU ointment and 5 hours after the application. To the skin in the dorsal region of each model mouse, the BU ointment further was applied twice a day for 6 days. Then, the skin in the dorsal region was observed on Day 6 from the start of the application and Day 6 after the stop of the application (Day 12 from the start of the application). Also, as a control, the skin in the dorsal region was observed in the same manner except that the control ointment used in the above item (2) was applied to the model mice (n=3) having the induced atopic dermatitis instead of the BU ointment.

Figure 17:
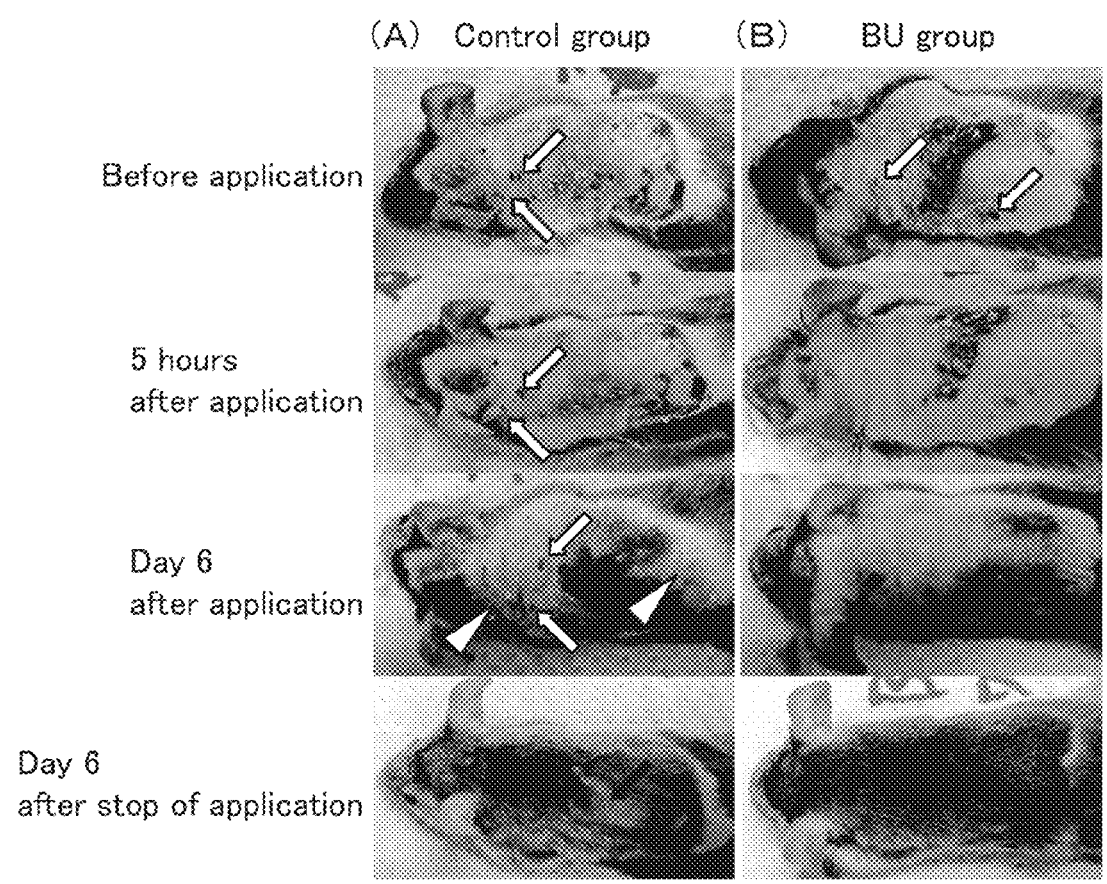
FIGS. 17A and 17B each show photographs of the skin in a dorsal region of an atopic dermatitis model mouse in Example 4.

The results thereof are shown in FIG. 17. FIG. 17 shows photographs of the skins in the dorsal regions of the model mice. FIG. 17A shows the model mouse to which the control ointment was applied (in the control group). FIG. 17B shows the model mouse to which the BU ointment was applied (in the BU group). In both FIGS. 17A and 17B, the photographs show, from the top, the result obtained before the application, the result obtained 5 hours after the application, the result obtained on Day 6 from the start of the application, and the result obtained on Day 6 after the stop of the application.

Before the application of the BU ointment or the control ointment, as can be seen from the first row in FIGS. 17A and 17B, bleeding (indicated with the open arrows) and projections of the epidermis (eruptions) were observed on the skin in the dorsal region of the model mice. Then, as can be seen from FIG. 17A, in the control group to which the control ointment had been applied, bleedings were observed (indicated with open arrows) even 5 hours after the application, as can be seen from the 2nd row; skin desquamation was observed (indicated with arrowhead figures) on Day 6 from the start of the application, as can be seen from the 3rd row; and a large nonhairy part (indicated with the black arrow) remained on Day 6 after the stop of the application, as can be seen from the 4th row. In contrast, as can be seen from FIG. 17B, in the BU group to which the BU ointment had been applied, bleeding was inhibited and the eruption disappeared 5 hours after the application, as can be seen from the 2nd row; skin desquamation was not observed on Day 6 from the start of the application, as can be seen from the 3rd row; and the entire dorsal region was covered with hair on Day 6 after the stop of the application, as can be seen from the 4th row. Although FIG. 17 shows the result obtained regarding one mouse in each of the control group and the BU group, similar results were obtained regarding the remaining model mice. These results demonstrate that bromovalerylurea can treat allergic dermatitis such as atopic dermatitis.

While the present invention has been described above with reference to embodiments and examples, the present invention is by no means limited thereto. Various changes and modifications that may become apparent to those skilled in the art may be made in the configuration and specifics of the present invention without departing from the scope of the present invention.

This application claims priority from Japanese Patent Application No. 2012-173405 filed on Aug. 3, 2012. The entire disclosure of this Japanese patent application is incorporated herein by reference.

INDUSTRIAL APPLICABILITY

As specifically described above, according to the present invention, activation of immune cells can be inhibited by the presence of bromovalerylurea. Because bromovalerylurea can inhibit the activation of immune cells as described above, it can be used in, for example, treatment of neurological diseases involving neuron death or treatment of inflammatory diseases. Thus, it can be said that the present invention is very useful in the field of pharmaceuticals.

The invention claimed is:

1. A method for treating an inflammatory disease, the method comprising a step of:
   administering transdermally to a subject a pharmaceutical of treating an inflammatory disease in an effective amount thereof,
   wherein an active ingredient exhibiting an anti-inflammatory activity in the pharmaceutical consists of: bromovalerylurea or a hydrate, solvate, isomer or a salt thereof, and
   the pharmaceutical is in a form of ointment, cream, or lotion for the transdermal administration.

2. The method for treating an inflammatory disease according to claim 1, wherein the inflammatory disease is an inflammatory skin disease.

3. The method for treating an inflammatory disease according to claim 2,
   wherein the inflammatory skin disease is at least one disease selected from the group consisting of atopic dermatitis, contact dermatitis, psoriasis, eczema, diaper dermatitis, seborrheic dermatitis, lichen simplex chronicus Vidal, autosensitization dermatitis, senile xerosis, actinic dermatitis, bullous diseases, keloid, erythroderma, drug eruption, and toxicoderma.

* * * * *